United States Patent
Reid et al.

(10) Patent No.: US 11,384,116 B2
(45) Date of Patent: Jul. 12, 2022

(54) METHODS OF MAKING CHOLIC ACID DERIVATIVES AND STARTING MATERIALS THEREFOR

(71) Applicant: Sandhill One, LLC, West Palm Beach, FL (US)

(72) Inventors: J. Gregory Reid, Wellington, FL (US); Jayachandra P Reddy, West Palm Beach, FL (US); Bernhard J. Paul, Arlington, MA (US); Sk Samad Hossain, Hyderabad (IN)

(73) Assignee: Sandhill One, LLC, West Palm Beach, FL (US)

( * ) Notice: Subject to any disclaimer, the term of this patent is extended or adjusted under 35 U.S.C. 154(b) by 0 days.

(21) Appl. No.: 17/399,105

(22) Filed: Aug. 11, 2021

(65) Prior Publication Data
US 2022/0056070 A1  Feb. 24, 2022

Related U.S. Application Data

(60) Provisional application No. 63/068,498, filed on Aug. 21, 2020.

(51) Int. Cl.
  *C07J 9/00*  (2006.01)
  *C07J 41/00*  (2006.01)

(52) U.S. Cl.
  CPC ............ *C07J 41/0061* (2013.01); *C07J 9/005* (2013.01)

(58) Field of Classification Search
  CPC .............................. C07J 9/005; C07J 41/0061
  See application file for complete search history.

(56) References Cited

U.S. PATENT DOCUMENTS

| | | |
|---|---|---|
| 5,595,996 A | 1/1997 | Graham et al. |
| 10,465,171 B2 | 11/2019 | Liu et al. |
| 2006/0252948 A1 | 11/2006 | Takehara et al. |

FOREIGN PATENT DOCUMENTS

| | | |
|---|---|---|
| CN | 111072744 A | 4/2020 |
| EP | 0230085 A1 | 7/1987 |
| WO | 2017/019524 A1 | 2/2017 |
| WO | 2017/079062 A1 | 5/2017 |
| WO | 2021/109791 A1 | 6/2021 |

OTHER PUBLICATIONS

Fantin, Giancarlo et al., Synthesis of 7- and 12-Hydroxy-and 7,12-Dihydroxy-3-Keto-5B-Cholan-24-Oic Acids by Reduction of 3,7-, 3,12- and 3,7,12-Oxo Derivatives, Steroids, 1993, vol. 58, November, pp. 524-526.

He, Xiao-Long et al., A Facile Synthesis of Ursodeoxycholic Acid and Obeticholic Acid From Cholic Acid, Elsevier, Steroids 140 (2018) 173-178.

Mappus, E., et al., Synthesis and Stereochemistry of C-3- and C-7-Linked (O-Carboxymethyl)-Oximino- and Hemisuccinamido Derivatives of 5a-Dihydrotestosterone, Steroids, Jun. 1979, vol. 33, No. 6, 26 pp.

Ocaliva® (obeticholic acid) tablets, for oral use, Highlights of Prescribing Information, revised Feb. 2020, 22 pp.

Salen, Gerald, et al., Effect of 7-Ketolithocholic Acid on Bile Acid Metabolism in Humans, Gastroenterology 1982;83:341-7.

Samaja, Gisela A., et al., 27-Nor-Δ4-dafachronic acid is a synthetic ligand of Caenorhabditis elegans DAF-12 receptor, Elsevier, Bioorganic & Medicinal Chemistry Letters 23 (2013) 2893-2896.

Product Monograph, URSOPrURSO® 250 mg Tablets, PrURSO DS® 500 mg Tablets, ursodiol tablets, USP, Bile Acid Preparation, A05AA02, Aptalis Pharma Canada Inc., Date of Preparation: Nov. 2, 2011, Date of Revision: Aug. 18, 2014, 28 pp.

Wang, Jie et al., Synthesis of ursodeoxycholic acid from plant-source (20S)-21-hydroxy-20-methylpregn-4-en-3-one, Elsevier, Steroids 157 (2020) 108600, 2020, 6 pp.

Sandhill One, LLC; International Application No. PCT/US2021/045467 filed Aug. 11, 2021; International Search Report and Written Opinion, ISA/US; dated Feb. 8, 2022; 15 pp.

Li et al.; Bile Acid Derivatives From a Sponge-Associated Bacterium *Psychrobacter* sp.; Archives of Pharmacal Research, Jun. 26, 2009 (Jun. 26, 2009), vol. 32, pp. 857-862; p. 858.

*Primary Examiner* — Barbara P Badio
(74) *Attorney, Agent, or Firm* — Clark G. Sullivan

(57) ABSTRACT

Methods of making cholic acid derivatives, particularly ursodeoxycholic acid, tauroursodeoxycholic acid, 7-ketolithocholic acid, obeticholic acid, their carboxylate salts and carboxylate esters, and starting materials and intermediates therefor.

17 Claims, No Drawings

METHODS OF MAKING CHOLIC ACID DERIVATIVES AND STARTING MATERIALS THEREFOR

FIELD OF THE INVENTION

The present invention relates generally to methods of making cholic acid derivatives, particularly ursodeoxycholic acid, tauroursodeoxycholic acid, 7-ketolithocholic acid, obeticholic acid, their carboxylate salts and carboxylate esters, and starting materials and intermediates therefor.

BACKGROUND OF THE INVENTION

Cholic acid and its derivatives find utility in numerous medical applications and research initiatives. Cholic acid itself, sold under the brand name CHOLBAM® (cholic acid), is approved for use as a treatment for children and adults with bile acid synthesis disorders due to single enzyme defects, and for peroxisomal disorders (such as Zellweger syndrome). 7-Ketolithocholic acid has been examined for its effect on endogenous bile acid synthesis, biliary cholesterol saturation, and its possible role as a precursor of chenodeoxycholic acid and ursodeoxycholic acid. See Salen et al. Gasteroenterology, 1982; 83:341-7. Ursodeoxycholic acid (a/k/a UDCA or ursodiol), sold under the brand name URSO 250® and URSO FORTE® tablets (ursodiol), is approved for the treatment of patients with primary biliary cirrhosis (PBC). More recently, obeticholic acid, sold under the brand name OCLAVIA® (obeticholic acid), was approved for the treatment of PBC in combination with UDCA in adults with an inadequate response to UDCA, or as monotherapy in adults unable to tolerate UDCA.

In spite of this significant medical interest in cholic acid derivatives, methods of synthesizing the derivatives remain a cumbersome inefficient process, with numerous processes being proposed. Fantin et al. Steroids, 1993 November; 58:524-526, discloses the preparation of 7α-, 12α-, 12β-hydroxy and 7α-,12α- and 7α-,12β-dihydroxy-3-keto-cholanoic acids by protecting the 3-keto group as dimethyl ketal and subsequent reduction with sodium borohydride of the corresponding 7- and 12-oxo functionalities. WO 2017/079062 A1 by Galvin reports a method of preparing obeticholic acid by direct alkylation at the C-6 position of 7-keto lithocholic acid (KLCA). He et al., Steroids, 2018 December; 140:173-178, discloses a synthetic route of producing ursodeoxycholic acid (UDCA) and obeticholic acid (OCA) through multiple reactions from cheap and readily-available cholic acid. Wang et al., Steroids 157 (2020) 108600, similarly report a synthetic route of producing ursodeoxycholic acid (UDCA) through multiple reactions from commercially available bisnoralcohol (BA).

What is needed are more efficient processes for making cholic acid derivatives, including starting materials and intermediates therefor. Particularly needed are more efficient processes for making ursodeoxycholic acid, tauroursodeoxycholic acid, 7-ketolithocholic acid, obeticholic acid, their carboxylate salts and carboxylate esters, and starting materials and intermediates therefor.

SUMMARY OF INVENTION

In a first aspect the invention provides compounds useful as intermediates in the synthesis or fermentation of cholic acid derivatives having 5α or 5β stereochemistry. Thus, in a first principal embodiment the invention provides a compound of Formula I:

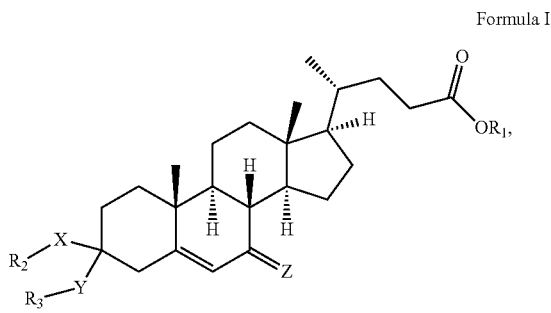

Formula I or a carboxylate salt thereof, wherein: (a) X is oxy, thio, or $N(R_4)$; (b) Y is oxy or thio; (c) Z is oxo; (d) $R_1$ is hydrogen, a counterion when the compound is a carboxylate salt, optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In another aspect, the invention provides compounds useful as intermediates in the synthesis or fermentation of cholic acid derivatives having 5α stereochemistry. Thus, in a second principal embodiment the invention provides a compound of Formula II:

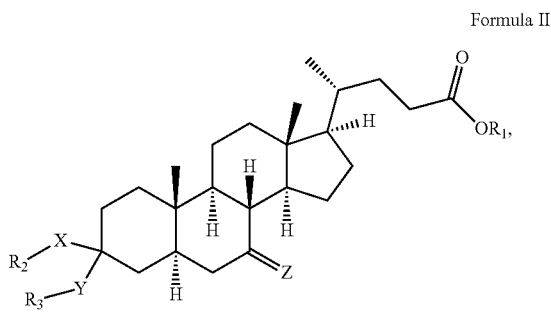

Formula II or a carboxylate salt thereof, wherein: (a) X is oxy, thio, or $N(R_4)$; (b) Y is oxy or thio; (c) Z is oxo; (d) $R_1$ is hydrogen, a counterion when the compound is a carboxylate salt, optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In still another aspect the invention provides compounds useful as intermediates in the synthesis or fermentation of cholic acid derivatives having 5β stereochemistry. Thus, in a third principal embodiment the invention provides a compound of Formula III:

Formula III

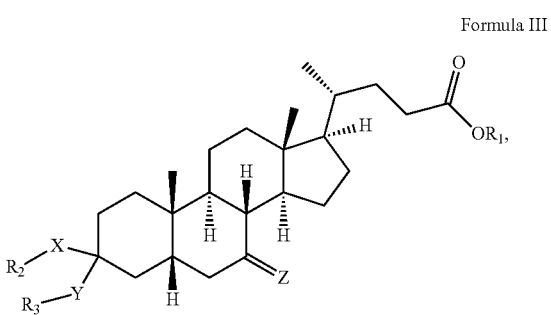

wherein: (a) X is oxy, thio, or N($R_4$); (b) Y is oxy or thio; (c) Z is oxo; (d) $R_1$ is optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In a fourth principal embodiment the invention provides a compound of Formula IIIa or Formula IIIb:

Formula IIIa

Formula IIIb

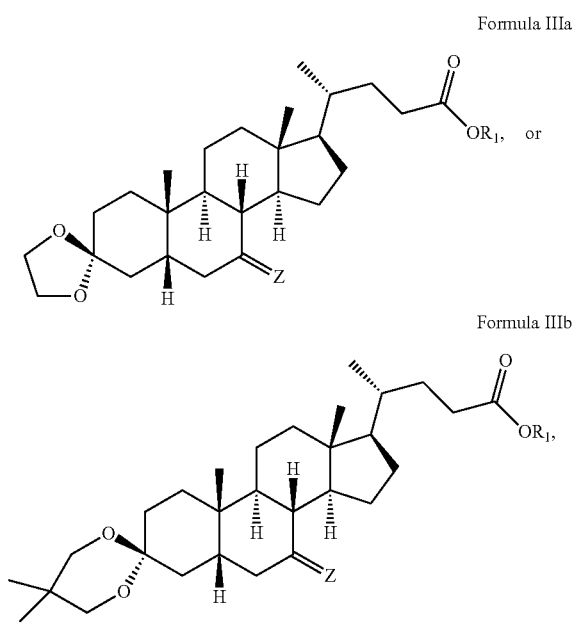

or a carboxylate salt thereof, wherein: (a) Z is oxo; and (b) $R_1$ is hydrogen, a counterion when the compound is a carboxylate salt, optionally substituted $C_{1-20}$ alkyl, or optionally substituted aryl.

Still further embodiments relate to methods for converting the 5β, 7-keto or 5,6-dehydro, 7-keto, compounds of the current invention to cholic acid derivatives. Thus, in a fifth principal embodiment the invention provides a method of converting any of the 5β, 7-keto or 5,6-dehydro, 7-keto compounds of the current invention to ursodeoxycholic acid or a carboxylate salt at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to give a 3-ketone; (c) reducing the 3-ketone to a 3α-hydroxyl; (d) reducing the 7-ketone to a 7β-hydroxyl; and (e) when $R_1$ is alkyl or aryl, hydrolyzing the —$CO_2R_1$ ester to a carboxylic acid; wherein steps (a)-(e) may be carried out sequentially, simultaneously, or in any order, except that step (b) must be performed before step (c).

In a sixth principal embodiment the invention provides a method of converting any of the 5β, 7-keto or 5,6-dehydro, 7-keto compounds of the current invention to 7-ketolithocholic acid or an ester or carboxylate salt thereof at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to give a 3-ketone; (c) reducing the 3-ketone to a 3α-hydroxyl; and (d) when $R_1$ is alkyl or aryl, optionally hydrolyzing the —$CO_2R_1$ ester to a carboxylic acid; wherein steps (a)-(d) may be carried out sequentially, simultaneously, or in any order, except that step (b) must be performed before step (c).

In a seventh principal embodiment the invention provides a method of converting any of the 5β, 7-keto or 5,6-dehydro, 7-keto compounds of the current invention to obeticholic acid or an ester or carboxylate salt thereof at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to give a 3-ketone; (c) reducing the 3-ketone to a 3α-hydroxyl; (d) reacting with lithium diisopropylamide and chlorotrimethylsilane to form an enol silane at the 6,7-position; (e) reacting with acetaldehyde and boron trifluoride-etherate to give an ethylidene group at the 6-position; (f) when $R_1$ is alkyl or aryl, hydrolyzing the —$CO_2R_1$ ester to a carboxylic acid; (g) reacting with hydrogen and a palladium-on-carbon catalyst to produce 6α-ethyl; and (h) reducing the 7-ketone to a 7α-hydroxyl, for example by reacting with sodium borohydride.

In an eighth principal embodiment the invention provides a method of converting any of the 5 β, 7-keto or 5,6-dehydro, 7-keto compounds of the current invention to tauroursodeoxycholic acid ("TUDCA") or a pharmaceutically acceptable salt thereof, comprising: (a) when a 5,6-alkene double bond is present, reducing the 5,6-alkene double bond to a dihydro product with 5β stereochemistry; (b) hydrolyzing the electronegative groups at the 3-position to produce a 3-ketone; (c) reducing the 3-ketone to 3α-hydroxyl; (d) reducing the 7-ketone to 7ß-hydroxyl; and (e) converting the 24-carboxylic acid or ester group to a derivative that can act as an acylating agent, and (f) reacting the derivative with taurine to form TUDCA or a pharmaceutically acceptable salt thereof, wherein steps (a)-(f) may be carried out sequentially, simultaneously or in any order except that step (b) must be performed before step (c), and step (e) must be performed before step (f).

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Definitions and Use of Terms

As used in the specification and claims, the singular forms a, an, and the include plural references unless the context clearly dictates otherwise. For example, the term "a specification" refers to one or more specifications for use in the presently disclosed methods and systems. "A hydrocarbon" includes mixtures of two or more such hydrocarbons, and the like. The word "or" or like terms as used herein means any one member of a particular list and also includes any combination of members of that list.

As used in this specification and in the claims which follow, the word "comprise" and variations of the word, such as "comprising" and "comprises," means "including but not limited to," and is not intended to exclude, for example, other additives, components, integers or steps. When an element is described as comprising one or a plurality of components, steps or conditions, it will be understood that the element can also be described as "consisting of" or "consisting essentially of" the component, step or condition, or the plurality of components, steps or conditions.

When used herein the term "about" will compensate for variability allowed for in the pharmaceutical industry and inherent in pharmaceutical products. In one embodiment the term allows for any variation within 5% of the recited specification or standard. In one embodiment the term allows for any variation within 10% of the recited specification or standard.

Ursodeoxycholic acid, 3α,7β-dihydroxy-5β-cholanic acid, or simply ursodiol or UDCA, is an epimer of chenodeoxycholic acid having the following chemical structure:

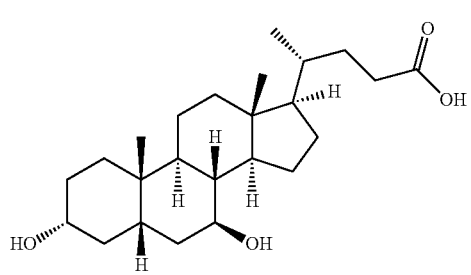

Tauroursodeoxycholic acid, or TUDCA, has the following chemical structure:

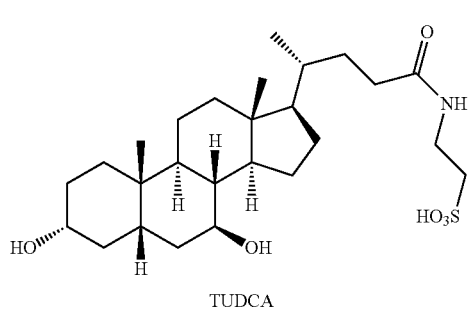

TUDCA

Obeticholic acid, or 3α,7α-dihydroxy 6α-ethyl-5β-cholan-24-oic acid, has the following chemical structure:

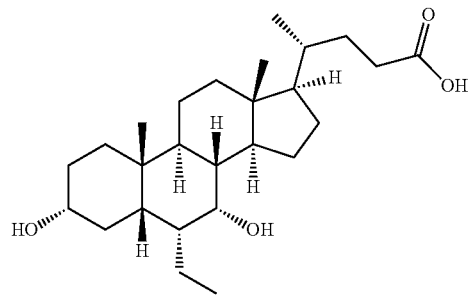

7-ketolithochoic acid, or 3α-hydroxy-7-keto-5β-cholanic acid, has the following chemical structure:

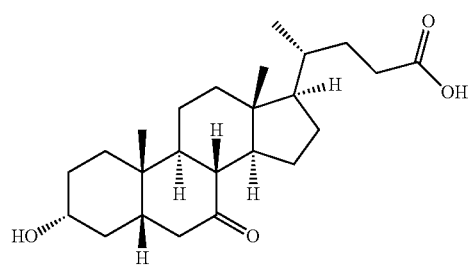

KCEA, or 3-ketochol-4-enoic acid, has the following chemical structure:

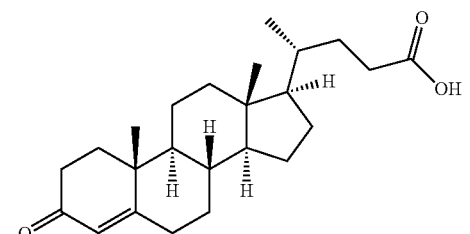

Discussion

In a first principal embodiment the invention provides a compound of Formula I:

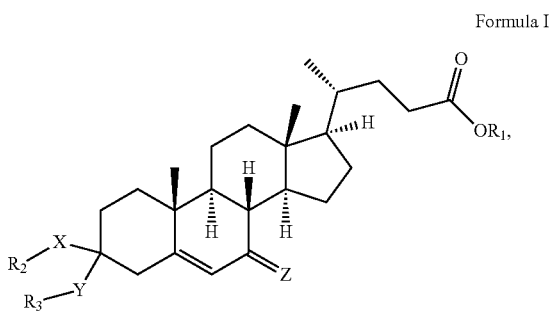

Formula I or a carboxylate salt thereof, wherein: (a) X is oxy, thio, or $N(R_4)$; (b) Y is oxy or thio; (c) Z is oxo; (d) $R_1$ is hydrogen, a counterion when the compound is a carboxylate salt, optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In a preferred subembodiment of this first principal embodiment, X is oxy and Y is oxy (subembodiment 1a). In another preferred subembodiment of this first principal embodiment, X is oxy, Y is oxy, and $R_2$ and $R_3$ are joined to form with X and Y a spirofused heterocyclic ring at the 3-position of Formula I, preferably a cyclic ketal (substituted or unsubstituted) in which the 3-carbon is the ketal carbon (subembodiment 1d).

Additional subembodiments related to the first principal embodiment are defined by Formula Ia and Formula Ib, in which $R_2$ and $R_3$ are joined to form with X and Y a spirofused heterocyclic ring at the 3-position of Formula I. In particular, they are joined to form a cyclic ketal at the 3-position of Formula I, as depicted in Formulas Ia and Ib:

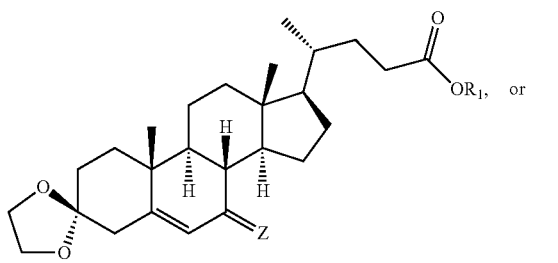

Formula Ia

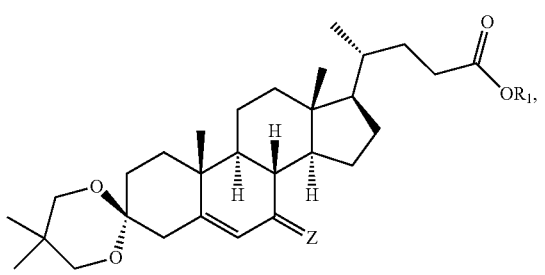

Formula Ib or a carboxylate salt thereof, wherein Z is oxo and $R_1$ is hydrogen or $C_{1-20}$ alkyl or a counterion when the compound is a carboxylate salt (subembodiment 1g).

Preferred subembodiments are defined when:

The compound is represented by Formula Ia, and $R_1$ is methyl (subembodiment 1h).

The compound is represented by Formula Ia, and $R_1$ is ethyl (subembodiment 1i).

The compound is represented by Formula Ia, and $R_1$ is hydrogen (subembodiment 1j).

The compound is a carboxylate salt of Formula Ia, and $R_1$ is a counterion (subembodiment 1k).

The compound is represented by Formula Ia, and $R_1$ is optionally substituted $C_{1-20}$ alkyl, or optionally substituted aryl (subembodiment 1l).

The compound is represented by Formula Ib, and $R_1$ is methyl (subembodiment 1m).

The compound is represented by Formula Ib, and $R_1$ is ethyl (subembodiment 1n).

The compound is represented by Formula Ib, and $R_1$ is hydrogen (subembodiment 1o).

The compound is a carboxylate salt of Formula Ib, and $R_1$ is a counterion (subembodiment 1p).

The compound is represented by Formula Ib, and $R_1$ is optionally substituted $C_{1-20}$ alkyl, or optionally substituted aryl (subembodiment 1q).

In a second principal embodiment the invention provides a compound of Formula II:

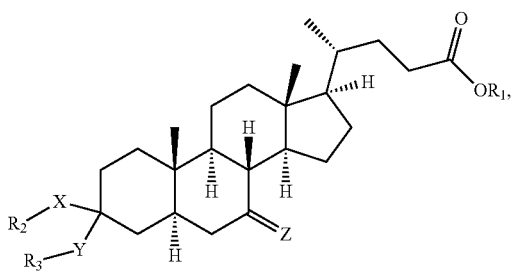

Formula II or a carboxylate salt thereof, wherein: (a) X is oxy, thio, or $N(R_4)$; (b) Y is oxy or thio; (c) Z is oxo; (d) $R_1$ is hydrogen, a counterion when the compound is a carboxylate salt, optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In a preferred subembodiment of this second principal embodiment, X is oxy and Y is oxy (subembodiment 2a). In another preferred subembodiment of this second principal embodiment, X is oxy, Y is oxy, and $R_2$ and $R_3$ are joined to form with X and Y a spirofused heterocyclic ring at the 3-position of Formula I, preferably a cyclic ketal (substituted or unsubstituted) in which the 3-carbon is the ketal carbon (subembodiment 2b).

Additional subembodiments related to the second principal embodiment are defined by Formula IIa and Formula IIb, in which $R_2$ and $R_3$ are joined to form with X and Y a spirofused heterocyclic ring at the 3-position of Formula II. In particular, they are joined to form a cyclic ketal at the 3-position of Formula II, as depicted in Formulas IIa and IIb:

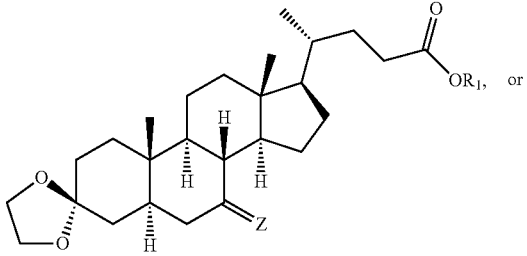

Formula IIa

-continued

Formula IIb

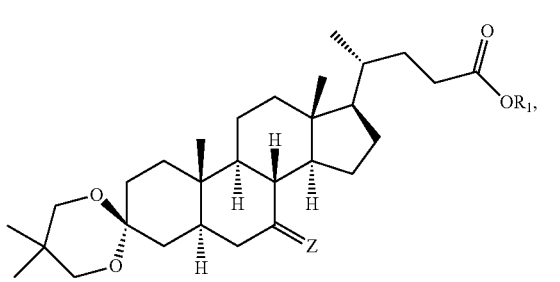

or a carboxylate salt thereof, wherein $R_1$ is hydrogen or $C_{1-20}$ alkyl or a counterion when the compound is a carboxylate salt (subembodiment 2c).

Preferred subembodiments are defined when:
The compound is represented by Formula IIa, and $R_1$ is methyl (subembodiment 2d).
The compound is represented by Formula IIa, and $R_1$ is ethyl (subembodiment 2e).
The compound is represented by Formula IIa, and $R_1$ is hydrogen (subembodiment 2f).
The compound is a carboxylate salt of Formula IIa, and $R_1$ is a counterion (subembodiment 2g).
The compound is represented by Formula IIa, and $R_1$ is optionally substituted $C_{1-20}$ alkyl, or optionally substituted aryl (subembodiment 2h).
The compound is represented by Formula IIb, and $R_1$ is methyl (subembodiment 2i).
The compound is represented by Formula IIb, and $R_1$ is ethyl (subembodiment 2j).
The compound is represented by Formula IIb, and $R_1$ is hydrogen (subembodiment 2k).
The compound is a carboxylate salt of Formula IIb, and $R_1$ is a counterion (subembodiment 2l).
The compound is represented by Formula IIb, and $R_1$ is optionally substituted $C_{1-20}$ alkyl, or optionally substituted aryl (subembodiment 2m).

In a third principal embodiment the invention provides a compound of Formula III:

Formula III

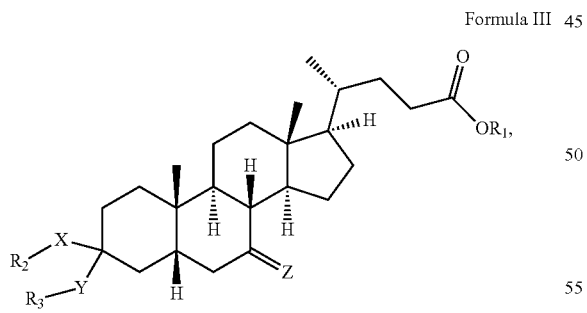

wherein: (a) X is oxy, thio, or $N(R_4)$; (b) Y is oxy or thio; (c) Z is oxo; (d) $R_1$ is optionally substituted $C_{1-20}$ alkyl, or optionally substituted aryl; (e) $R_2$, and $R_3$ are independently selected from optionally substituted $C_{1-20}$ alkyl and optionally substituted aryl; (f) $R_2$ and $R_3$ optionally are joined to form with X and Y a spirofused heterocyclic ring at the 3-position of Formula I; and (g) $R_4$ is H, optionally substituted $C_{1-20}$ alkyl, or optionally substituted aryl.

In a preferred subembodiment of this third principal embodiment, X is oxy and Y is oxy (subembodiment 3α). In another preferred subembodiment of this third principal embodiment, X is oxy, Y is oxy, and $R_2$ and $R_3$ are joined to form with X and Y a spirofused heterocyclic ring at the 3-position of Formula I, preferably a ketal (subembodiment 3b).

In a fourth principal embodiment the invention provides a compound of Formula IIIa or Formula IIIb:

Formula IIIa

Formula IIIb

or a carboxylate salt thereof, wherein: (a) Z is oxo; and (b) $R_1$ is hydrogen, a counterion when the compound is a carboxylate salt, optionally substituted $C_{1-20}$ alkyl, or optionally substituted aryl.

Preferred subembodiments are defined when:
The compound is represented by Formula IIIa, and $R_1$ is methyl (subembodiment 3d).
The compound is represented by Formula IIIa, and $R_1$ is ethyl (subembodiment 3e).
The compound is represented by Formula IIIa, and $R_1$ is hydrogen (subembodiment 3f).
The compound is a carboxylate salt of Formula IIIa, and $R_1$ is a counterion (subembodiment 3g).
The compound is represented by Formula IIIa, and $R_1$ is optionally substituted $C_{1-20}$ alkyl, or optionally substituted aryl (subembodiment 3h).
The compound is represented by Formula IIIb, and $R_1$ is methyl (subembodiment 3i).
The compound is represented by Formula IIIb, and $R_1$ is ethyl (subembodiment 3j).
The compound is represented by Formula IIIb, and $R_1$ is hydrogen (subembodiment 3k).
The compound is a carboxylate salt of Formula IIIb, and $R_1$ is a counterion (subembodiment 3l).
The compound is represented by Formula IIIb, and $R_1$ is optionally substituted $C_{1-20}$ alkyl, or optionally substituted aryl (subembodiment 3m).

Further embodiments relate to methods of making useful cholic acid derivatives from the 5β, 7-keto or 5,6-dehydro, 7-keto compounds of the current invention, including UDCA, 7-ketolithocholic acid, or obeticholic acid. The methods can be carried out based on well-known chemical reactions under conditions well known in the art, as described, for example, in March's Advanced Organic Chemistry: Reactions, Mechanisms, and Structure, by Michael B. Smith and Jerry March (Wiley-Interscience, 6th edition, 2007).

Therefore, in a fifth principal embodiment the invention provides a method of converting any of the 5β, 7-keto or 5,6-dehydro, 7-keto compounds of the current invention to ursodeoxycholic acid or a carboxylate salt at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to produce a 3-ketone; (c) reducing the 3-ketone to 3α-hydroxyl; (d) reducing the 7-ketone to 7β-hydroxyl; and (e) when $R_1$ is alkyl or aryl, hydrolyzing the —$CO_2R_1$ ester to a carboxylic acid; wherein steps (a)-(e) may be carried out sequentially, simultaneously, or in any order, except that step (b) must be performed before step (c).

Optionally, the UDCA can be further converted to TUDCA. Thus, the fifth principal embodiment may further comprise converting the 24-carboxylic acid or ester group to a derivative that can act as an acylating agent, and reacting the derivative with taurine to form TUDCA or a pharmaceutically acceptable salt thereof.

In various subembodiments of the fifth principal embodiment, the 5β, 7-keto or 5,6-dehydro, 7-keto compounds used as a starting material in this fifth principal embodiment is represented by a compound of the first principal embodiment, a compound of subembodiment 1a, a compound of subembodiment 1d, a compound of subembodiment 1g, a compound of subembodiment 1h, a compound of subembodiment 1i, a compound of subembodiment 1j, a compound of subembodiment 1k, a compound of subembodiment 1l, a compound of subembodiment 1m, a compound of subembodiment 1n, a compound of subembodiment 1o, a compound of subembodiment 1p, a compound of subembodiment 1q, a compound of the third principal embodiment, a compound of subembodiment 3a, a compound of subembodiment 3b, a compound of the fourth principal embodiment, a compound of subembodiment 3c, a compound of subembodiment 3d, a compound of subembodiment 3e, a compound of subembodiment 3f, a compound of subembodiment 3g, a compound of subembodiment 3h, a compound of subembodiment 3i, a compound of subembodiment 3j, a compound of subembodiment 3k, a compound of subembodiment 3l, a compound of subembodiment 3m, or any combination thereof.

In a sixth principal embodiment the invention provides a method of converting any of the 5β, 7-keto or 5,6-dehydro, 7-keto compounds of the current invention to 7-ketolithocholic acid or an ester or carboxylate salt thereof at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to produce a 3-ketone; (c) reducing the 3-ketone to 3α-hydroxyl; and (d) when $R_1$ is alkyl or aryl, optionally hydrolyzing the —$CO_2R_1$ ester to a carboxylic acid; wherein steps (a)-(d) may be carried out sequentially, simultaneously, or in any order, except that step (b) must be performed before step (c).

In various subembodiments of the sixth principal embodiment, the 5β, 7-keto or 5,6-dehydro, 7-keto compounds used as a starting material in this sixth principal embodiment is represented by a compound of the first principal embodiment, a compound of subembodiment 1a, a compound of subembodiment 1d, a compound of subembodiment 1g, a compound of subembodiment 1h, a compound of subembodiment 1i, a compound of subembodiment 1j, a compound of subembodiment 1k, a compound of subembodiment 1l, a compound of subembodiment 1m, a compound of subembodiment 1n, a compound of subembodiment 1o, a compound of subembodiment 1p, a compound of subembodiment 1q, a compound of the third principal embodiment, a compound of subembodiment 3a, a compound of subembodiment 3b, a compound of the fourth principal embodiment, a compound of subembodiment 3c, a compound of subembodiment 3d, a compound of subembodiment 3e, a compound of subembodiment 3f, a compound of subembodiment 3g, a compound of subembodiment 3h, a compound of subembodiment 3i, a compound of subembodiment 3j, a compound of subembodiment 3k, a compound of subembodiment 3l, a compound of subembodiment 3m, or any combination thereof.

In a seventh principal embodiment the invention provides a method of converting any of the 5β, 7-keto or 5,6-dehydro, 7-keto compounds of the current invention to obeticholic acid or an ester or carboxylate salt thereof at the 24-position thereof, comprising: (a) when a 5,6-alkene double bond is present, reducing the 5,6-alkene double bond to a dihydro product with 5β stereochemistry; (b) hydrolyzing the electronegative groups at the 3-position to produce a 3-ketone; (c) reducing the 3-ketone to 3α-hydroxyl; (d) reacting with lithium diisopropylamide and chlorotrimethylsilane to form an enol silane at the 6,7-position; (e) reacting with acetaldehyde and boron trifluoride-etherate to produce an ethylidene group at the 6-position; (f) when $R_1$ is alkyl or aryl, hydrolyzing the —$CO_2R_1$ ester to a carboxylic acid; (g) reacting with hydrogen and a palladium-on-carbon catalyst to produce 6α-ethyl; and (h) reducing the 7-ketone to 7α-hydroxyl, for example by reacting with sodium borohydride.

In various subembodiments of the seventh principal embodiment, the 5β, 7-keto or 5,6-dehydro, 7-keto compounds used as a starting material in this seventh principal embodiment is represented by a compound of the first principal embodiment, a compound of subembodiment 1a, a compound of subembodiment 1d, a compound of subembodiment 1g, a compound of subembodiment 1h, a compound of subembodiment 1i, a compound of subembodiment 1j, a compound of subembodiment 1k, a compound of subembodiment 1l, a compound of subembodiment 1m, a compound of subembodiment 1n, a compound of subembodiment 1o, a compound of subembodiment 1p, a compound of subembodiment 1q, a compound of the third principal embodiment, a compound of subembodiment 3a, a compound of subembodiment 3b, a compound of the fourth principal embodiment, a compound of subembodiment 3c, a compound of subembodiment 3d, a compound of subembodiment 3e, a compound of subembodiment 3f, a compound of subembodiment 3g, a compound of subembodiment 3h, a compound of subembodiment 3i, a compound of subembodiment 3j, a compound of subembodiment 3k, a compound of subembodiment 3l, a compound of subembodiment 3m, or any combination thereof.

In an eighth principal embodiment the invention provides a method of converting any of the 5β, 7-keto or 5,6-dehydro, 7-keto compounds of the current invention to tauroursodeoxycholic acid ("TUDCA") or a pharmaceutically acceptable salt thereof, comprising: (a) when a 5,6-alkene double bond is present, reducing the 5,6-alkene double bond to a dihydro product with 5β stereochemistry; (b) hydrolyzing the electronegative groups at the 3-position to produce a 3-ketone; (c) reducing the 3-ketone to 3α-hydroxyl; (d) reducing the 7-ketone to 7β-hydroxyl; and (e) converting the 24-carboxylic acid or ester group to a derivative that can act as an acylating agent, and (f) reacting the derivative with taurine to form TUDCA or a pharmaceutically acceptable salt thereof, wherein steps (a)-(f) may be carried out sequentially, simultaneously or in any order except that step (b) must be performed before step (c), and step (e) must be performed before step (f).

In various subembodiments of the eighth principal embodiment, the 5β, 7-keto or 5,6-dehydro, 7-keto compounds used as a starting material in this eighth principal embodiment is represented by a compound of the first principal embodiment, a compound of subembodiment 1a, a compound of subembodiment 1d, a compound of subembodiment 1g, a compound of subembodiment 1h, a compound of subembodiment 1i, a compound of subembodiment 1j, a compound of subembodiment 1k, a compound of subembodiment 1l, a compound of subembodiment 1m, a compound of subembodiment 1n, a compound of subembodiment 1o, a compound of subembodiment 1p, a compound of subembodiment 1q, a compound of the third principal embodiment, a compound of subembodiment 3a, a compound of subembodiment 3b, a compound of the fourth principal embodiment, a compound of subembodiment 3c, a compound of subembodiment 3d, a compound of subembodiment 3e, a compound of subembodiment 3f, a compound of subembodiment 3g, a compound of subembodiment 3h, a compound of subembodiment 3i, a compound of subembodiment 3j, a compound of subembodiment 3k, a compound of subembodiment 3l, a compound of subembodiment 3m, or any combination thereof.

As will be recognized by workers of skill in the art, the 5,6-alkene double bond can convert to a 4,5-alkene double bond when certain sequences of steps are observed, particularly when step (b) is performed before step (a) in any of the fifth through eighth principal embodiments, before the 5,6 double bond is fully reduced. In this situation, it will be understood that the 5,6-alkene double bond is reduced to a dihydro product with 5l3 stereochemistry, but that it occurs through the conversion to a 4,5-alkene double bond and the reduction of the 4,5-alkene double bond to a dihydro product with 5l3 stereochemistry.

Alternative Structural Subembodiments

In any of the embodiments or subembodiments of this invention, a moiety which is optionally substituted may be alternatively defined as substituted with 0, 1, 2, or 3 substituents independently selected from halo, OH, amine, $C_{1-6}$ alkyl, $C_{1-6}$ alkoxy, $C_{1-6}$ hydroxyalkyl, $CO(C_{1-6}$ alkyl), CHO, $CO_2H$, $CO_2(C_{1-6}$ alkyl), and $C_{1-6}$ haloalkyl.

A molecule which is optionally substituted also may be defined as substituted with 0, 1, 2, or 3 substituents independently selected from: halo, CN, OH, $NO_2$, $Si(CH_3)_4$, CHO, and $CO_2H$, or optionally substituted $CO(C_{1-6}$ alkyl), $CO_2(C_{1-6}$ alkyl), $NR^{10}R^{11}$, $NHCONR^{10}R^{11}$, $CONR^{10}R^{11}$, CH=NOH, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, and heterocycloalkyl (optionally substituted by halo, OH, amine, $C_{1-6}$ alkyl, $C_{1-6}$ alkoxy, $C_{1-6}$ hydroxyalkyl, $CO(C_{1-6}$ alkyl), CHO, $CO_2H$, $CO_2(C_{1-6}$ alkyl), or $C_{1-6}$ haloalkyl).

Any of the embodiments or subembodiments in which $R^{10}$ or $R^{11}$ are present can also be defined based on alternative Markush groups for $R^{10}$ and $R^{11}$. Thus, $R^{10}$ and $R^{11}$ can each independently be defined as H, $C_{1-6}$ alkyl, $CO(C_{1-6}$ alkyl), CO(heteroaryl), heteroaryl, or cycloalkyl. Alternatively, $R^{10}$ and $R^{11}$ can each independently be defined as H or $C_{1-6}$ alkyl.

Any of the embodiments or subembodiments in which $R_2$ and $R_3$ are present can also be defined based on alternative Markush groups for $R_2$ and $R_3$. Thus, in any of these embodiments or subembodiments $R_2$ and $R_3$ can be defined to be independently selected from: (a) H, CN, halo, CHO, or $CO_2H$, or (b) $C_{1-6}$ alkyl, $C_{1-6}$ hydroxyalkyl, $C_{1-6}$ alkylcycloalkyl, $C_{1-6}$ haloalkyl, $C_{1-6}$ alkoxy, $CO(C_{1-6}$ alkyl), $CO_2(C_{1-6}$ alkyl), or $CONR^{10}R^{11}$, any of which is optionally substituted, or (c) $R_2$ and $R_3$ can be joined to form with X and Y a spirofused heterocyclic ring at the 3-position of Formula I, II, or III.

Any of the embodiments or subembodiments in which $R_4$ is present can also be defined based on alternative Markush groups for $R_4$. Thus, in any of the embodiments or subembodiments of the invention, $R_4$ can be defined as H, $C_{1-6}$ alkyl, phenyl, OH, or $C_{1-6}$ alkoxy, wherein any of said $C_{1-6}$ alkyl, phenyl, or $C_{1-6}$ alkoxy is optionally substituted.

Chemical Definitions

A substituent is "substitutable" if it comprises at least one carbon, sulfur, oxygen or nitrogen atom that is bonded to one or more hydrogen atoms. Thus, for example, hydrogen, halogen, and cyano do not fall within this definition. If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent.

If a substituent is described as being "optionally substituted," the substituent may be either (1) not substituted, or (2) substituted. When a substituent is comprised of multiple moieties, unless otherwise indicated, it is the intention for the final moiety to serve as the point of attachment to the remainder of the molecule. For example, in a substituent A-B-C, moiety C is attached to the remainder of the molecule. If substituents are described as being "independently selected" from a group, each substituent is selected independent of the other. Each substituent therefore may be identical to or different from the other substituent(s).

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In any of the embodiments or subembodiments of the present invention, an alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "hydroxyalkyl" refers to an alkyl group having one or more OH substituents. Example hydroxyalkyl groups include $CH_2OH$, $C_2CH_4OH$, $C_3H_6OH$, and the like.

As used herein, "aryl" refers to monocyclic or polycyclic (e.g., having 2, 3 or 4 fused rings) aromatic hydrocarbons (including heteroaromatic hydrocarbons) such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups (including heterocycloalkyl). Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, cycloalkyl groups can have from about 3 to about 10, or about 3 to about 7 ring-forming carbon atoms.

As used herein, "heterocyclyl" or "heterocycle" refers to a saturated or unsaturated cyclic hydrocarbon wherein one or more of the ring-forming carbon atoms of the cyclic hydrocarbon is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-14 or 3-7 ring-forming atoms. In some embodiments, heterocyclyl groups can contain, in addition to at least one heteroatom, from about 1 to about 13, about 2 to about 10, or about 2 to about 7 carbon atoms and can be attached through a carbon atom or heteroatom. In further embodiments, the heteroatom can be oxidized (e.g., have an oxo substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10α-tetrahydro-1H-pyrazino[1,2-a]indol-2-yl, 1,2,4,4α,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6, 10b-hexahydro-2H-benzo[f]isoquinolin-3-yl, 3,3α, 8,8α-tetrahydro-1H-2-aza-cyclopenta[a]inden-2-yl, and 2,3,4,7-tetrahydro-1H-azepin-1-yl, azepan-1-yl.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyhc ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an —S-alkyl group.

As used here, "haloalkoxy" refers to an —O-haloalkyl group. An example haloalkoxy group is OCF.

As used herein, "cycloalkyloxy" refers to —O-cycloalkyl.

As used herein, "aralkyl" refers to an alkyl group substituted by an aryl group.

As used herein, "cycloalkylalkyl" refers to an alkyl group substituted by an cycloalkyl group.

As used herein, "heterocyclylalkyl" refers to an alkyl moiety substituted by a heterocarbocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein "oxo" refers to =O.

The compounds described herein can be asymmetric (e.g., having one or more stereocenters). The description of a compound without specifying its stereochemistry is intended to capture mixtures of stereoisomers as well as each of the individual stereoisomer encompassed within the genus.

The present invention also includes salts of the compounds described herein. As used herein, "salts" refers to derivatives of the disclosed compounds wherein the parent compound is modified by converting an existing acid or base moiety to its salt form. Examples of suitable salts include, but are not limited to, mineral or organic acid salts of basic residues such as amines; alkali or organic salts of acidic residues such as carboxylic acids; and the like. The salts of the present invention include the conventional non-toxic salts or the quaternary ammonium salts of the parent compound formed, for example, from non-toxic inorganic or organic acids. The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Finally, it will be understood that any of the novel compounds of the present invention (whether defined by a principal embodiment or a subembodiment or particular species) can be defined based on its purity and/or isolation from reaction media. Thus, in certain embodiments, the compounds are present in compositions at weight percentages greater than 10%, 50%, 90%, 95%, or 98%.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Synthesis of Compound 4a and 4b from KCEA

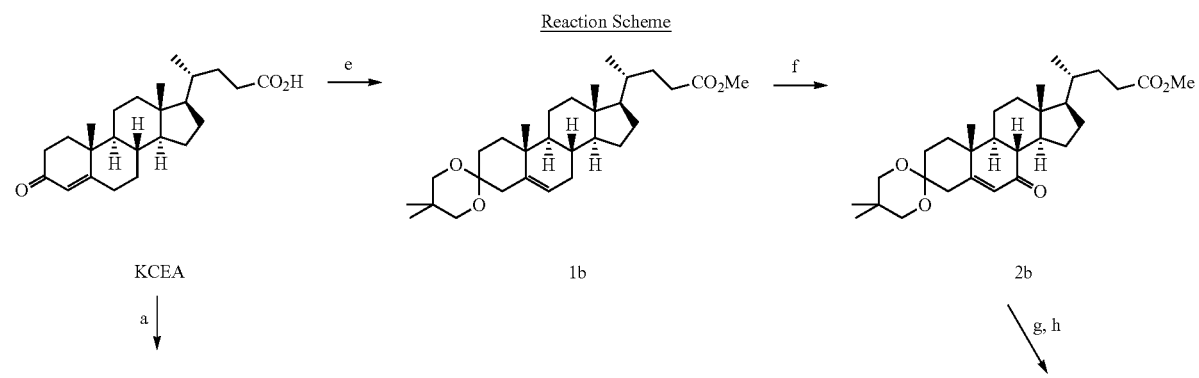

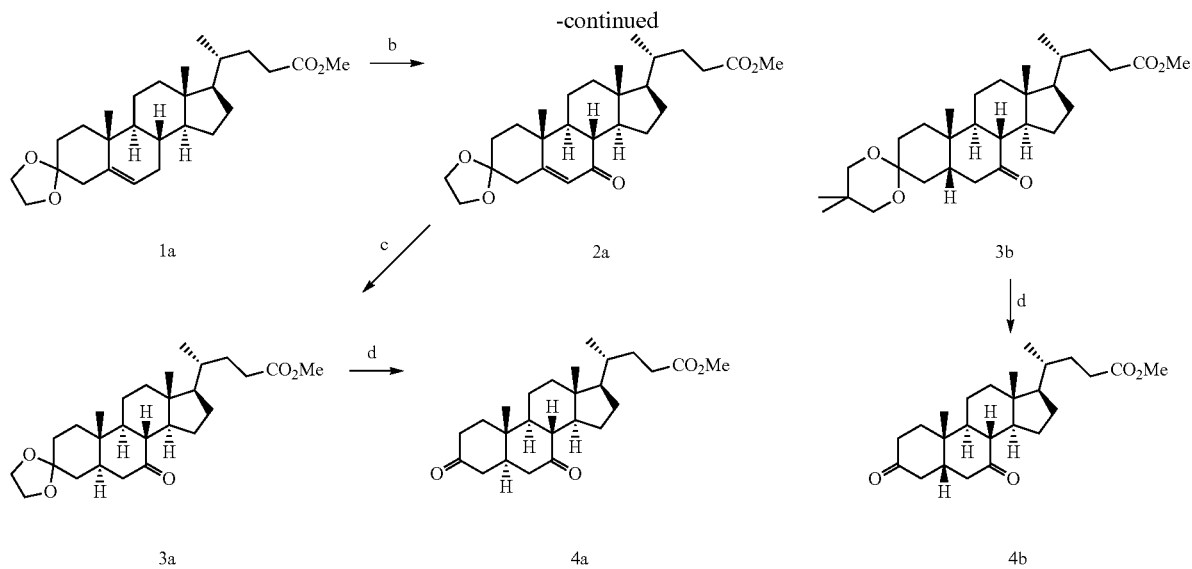

Reagents and conditions: (a) Methanol, trimethyl orthoformate, ethylene glycol, cat. p-toluenesulfonic acid, toluene, 50° C.;
(b) Cuprous iodide, t-butyl hydroperoxide, acetonitrile, 50° C.; (c) $H_2$, Pd/C, dioxane, 50° C.; (d) 80% aq. acetic acid, 100° C.;
(e) Methanol trimethyl orthoformate, 2,2-dimethyl-1,3-propanediol, cat. p-toluenesulfonic acid, toluene, 50° C.;
(f) N-Hydroxyphthalimide, pyridinium dichromate, acetonitrile, 25° C.; (g) $H_2$, $PtO_2$, isopropanol, 50° C.;
(h) Pyridinium chlorochromate, dichloromethane, 25° C.

Synthesis of Compound 1a from KCEA: A 250-mL round bottom flask equipped with a stirring bar and reflux condenser was charged with toluene (90 mL), methanol (10 mL) and KCEA (10 g, 26.842 mmol). The resulting solution was inerted with nitrogen and then trimethyl orthoformate (8.8 mL, 3 equiv.) and p-toluenesulfonic acid (0.5 g, 0.1 equiv.) were added sequentially. The resulting mixture was stirred at 50-55° C. for 1 h. The pressure was then reduced and ~20 mL of solvent was removed via distillation. Ethylene glycol (14.9 mL, 10 equiv.) and p-toluenesulfonic acid (0.5 g, 0.1 equiv.) were added and the reaction was continued for another 3 h. At this point the mixture was cooled to 5° C. in an ice bath and treated with aqueous sodium acetate solution (30 g in 150 mL water). The mixture was stirred for 1 h at 5° C. and the resulting suspension was filtered to obtain crude product. This was purified further by silica gel chromatography to obtain Compound 1a as a white solid (6.24 g, 54% yield). $^1$H NMR (400 MHz, DMSO-D6) δ 5.20 (s, 1H), 3.80 (m, 4H), 3.56 (s, 3H), 2.45-0.95 (m, 25H), 0.95 (s, 3H), 0.87 (d, J=8 Hz, 3H), 0.63 (S, H); ESIMS for $C_{27}H_{42}O_4$ m/z 431.8 [M+H]$^+$.

Synthesis of Compound 2α: A 50-mL round bottom flask equipped with a stirring bar and reflux condenser was charged with acetonitrile (3 mL) and Compound 1a (0.3 g, 0.69 mmol). Cuprous iodide (6.6 mg, 0.05 equiv.) and t-butyl hydroperoxide (0.71 mL, 70% solution in water, 8 equiv.) were added successively and the resulting reaction mixture was stirred at 50° C. for 24 h. The reaction mixture was cooled to 25° C. and quenched with saturated $Na_2SO_3$ solution. The product was extracted into EtOAc (2×10 mL) and concentrated under vacuum to obtain crude product, which was purified by silica gel chromatography to obtain Compound 2α as an off-white solid (90 mg, 29% yield). $^1$H NMR (400 MHz, $CDCl_3$) δ 5.66 (d, J=2 Hz, 1H), 4.0-3.91 (m, 4H), 3.66 (s, 3H), 245-1.05 (m, 22H), 1.30 (s, 3H), 0.93 (d, J=6 Hz, 3H), 0.68 (s, 3H); ESIMS for $C_{27}H_{40}O_5$ m/z 445.7 [M+H]$^+$.

Synthesis of Compound 3α: A 100 mL SS autoclave equipped with a stirring bar. 1,4-Dioxane (30 mL) and Compound 2α (600 mg, 1.35 mmol) were added at room temperature. $Pd(OH)_2$/C catalyst (300 mg, 50% water wet) was added and the resulting mixture was stirred under 100 psi hydrogen pressure at 50° C. for 30 h. At this point TLC analysis showed complete conversion, so the reaction mixture was filtered through a thin pad of CELITE® (silica) and the filtrate was concentrated to dryness under reduced pressure. GC analysis confirmed formation of 94.5% of the 5α-isomer (Compound 3α) and 5.5% of the 5β-isomer. The product mixture was purified by silica gel chromatography to obtain Compound 3α, as an off-white solid (350 mg, isolated yield: 58%). $^1$H NMR (400 MHz, $CDCl_3$): δ 3.85-3.95 (m, 3H), 3.67 (s, 3H), 2.43-2.18 (m, 8H), 2.06-0.88 (m, 24H), 0.66 (s, 3H); $^{13}$C NMR (100 MHz, $CDCl_3$): δ 211.2, 174.2, 108.2, 63.8, 63.7, 54.4, 54.2, 50.9, 49.4, 48.4, 45.3, 45.1, 42.1, 38.2, 37.3, 35.4, 34.7, 34.6, 30.6, 30.54, 30.5, 27.8, 24.5, 21.3, 17.9, 11.6, 10.5; ESIMS for $C_{27}H_{42}O_5$ m/z 447.6 [M+H]$^+$;

Synthesis of Compound 4α: A 50 mL round bottom flask equipped with a stirring bar and reflux condenser was charged with 80% aq. AcOH (7.2 mL, 24 vol) and Compound 3α (300 mg). The reaction mixture was stirred at 100° C. for 1 h and TLC analysis showed complete conversion of starting material. After completion, the reaction mixture was cooled to 0° C. and diluted with ice cold water (30 mL, 100 vol.), stirred for another 1 h and the resulting solid was collected by filtration. The crude product was purified by silica gel chromatography to obtain Compound 4α as white crystalline solid. (120 mg, 44%). $^1$H NMR (400 MHz, $CDCl_3$) δ 3.66 (s, 3H), 2.48-0.85 (m, 29H), 0.92 (d, J=6.3 Hz, 3H), 0.68 (s, 3H); ESIMS for $C_{25}H_{38}O_4$ m/z 420.6 [M+18]$^+$.

Synthesis of Compound 1b from KCEA: A 250 mL round bottom flask equipped with a stirring bar and reflux condenser was charged with toluene (90 mL), methanol (10 mL) and KCEA (10 g, 26.842 mmol). The resulting solution was inerted with nitrogen and then trimethyl orthoformate (8.8 mL, 3 equiv.) and p-toluenesulfonic acid (0.5 g, 0.1 equiv.) were added sequentially. The resulting mixture was stirred at 50-55° C. for 1 h. The pressure was then reduced and ~20 mL of solvent was removed via distillation. 2,2-Dimethyl-propane-1,3-diol (22.3 g, 8 equiv.) and p-toluenesulfonic acid (0.5 g, 0.1 equiv.) were added and the reaction was continued for another 3 h. At this point the mixture was cooled to 5° C. in an ice bath and treated with aqueous sodium acetate solution (30 g in 150 mL water). The mixture was stirred for 1 h at 5° C. and the resulting suspension was filtered to obtain crude product. This was purified further by silica gel chromatography to obtain Compound 1b as a white solid. (7.4 g, 59% yield). $^1$H NMR (400 MHz, CDCl3) δ 5.38-5.33 (m, 1H), 3.68 (s, 3H), 3.60, 3.50 (ABq, 2H, $J_{AB}$=11.2 Hz), 3.49-3.43 (m, 2h), 2.61-0.91 (m, 37H), 0.69 (s, 3H); ESIMS for $C_{30}H_{48}O_4$ m/z 473.6 [M+H]$^+$.

Synthesis of Compound 2b: A 250 mL round bottom flask equipped with a stirring bar and reflux condenser was charged with acetonitrile (140 mL, 20 vol) and Compound 1b (7.0 g, 14.8 mmol). N-Hydroxyphthalimide (NHPI, 2.89 g, 1.2 equiv.) and pyridinium dichromate (PDC, 16.71 g, 3.0 equiv.) were added successively at room temperature and the resulting solution was stirred at the same temperature for 4 h. Reaction completion was confirmed by TLC. The mixture was filtered through a thin pad of CELITE® (silica) and the filtrate was concentrated under reduced pressure. The residue was purified by silica gel chromatography to obtain Compound 2b as white solid (3.8 g, 52.7%). $^1$H NMR (400 MHz, CDCl$_3$) δ 5.68 (s, 1H), 3.65 (S, 3H), 3.58-3.49 (m, 2H), 3.41 (dd, J=18.4 Hz, 10 Hz, 2H), 2.83 (dd, J=14.8 Hz, 3.2 Hz, 1H), 2.48-0.89 (m, 34H), 0.67 (s, 3H); ESIMS for $C_{30}H_{46}O_5$ m/z 487.5 [M+H]$^+$.

Synthesis of Compound 3b: A 100 mL round bottom flask was equipped with a stirring bar and reflux condenser. Isopropanol (40 mL, 40 vol.) and Compound 2b (1 g, 2.055 mmol) were added at room temperature. PtO$_2$ catalyst (500 mg) was added and the resulting reaction mixture was stirred at 45-50° C. for 3 h under 5-10 psi of hydrogen. TLC analysis showed complete conversion of starting material, so the reaction mixture was cooled to room temperature and filtered through a thin pad of CELITE® (silica). The filtrate was concentrated to dryness under reduced pressure. The residue (1 g) was dissolved in dichloromethane (30 mL) and treated with pyridinium chlorochromate (PCC, 1.31 g) at room temperature. The resulting mixture was stirred for 3 h at room temperature, at which point TLC analysis showed two major products. GC analysis confirmed the formation of 55% of the 5β-isomer (Compound 3b) along with 45% of the 5α-isomer. The reaction mixture was filtered through a thin pad of CELITE® (silica) and the filtrate was concentrated to dryness under vacuum. The residue was purified by silica gel chromatography to obtain the Compound 3b as an off-white crystalline solid (90 mg). An additional 530 mg of a white solid that was a mixture of both isomers was also obtained. $^1$H NMR (400 MHz, CDCl$_3$): δ 3.66 (s, 3H), 3.52 (d, J=11.3 Hz, 1H), 3.47 (d, J=11.3 Hz, 1H), 3.42 (s, 2H), 2.83 (dd, J=12.5 Hz and 5.6 Hz, 1H), 2.42-0.78 (m, 37H), 0.68 (s, 3H); $^{13}$C NMR (100 MHz, CDCl$_3$): δ 211.7, 174.2, 97.4, 69.5, 69.4, 54.2, 51.0, 49.1, 48.4, 44.7, 43.4, 42.2, 41.9, 38.5, 35.1, 34.7, 33.0, 31.2, 30.6, 30.5, 29.7, 29.2, 27.8, 27.3, 24.3, 22.4, 22.3, 22.1, 21.4, 17.9, 11.6; ESIMS for $C_{30}H_{48}O_5$ m/z 489.8 [M+H]$^+$.

Synthesis of Compound 4b: To a 20 mL round bottom flask equipped with a stirring bar and reflux condenser was charged with 80% aq. AcOH (4.8 mL, 24 vol) and Compound 3b (200 mg). The reaction mixture was stirred at 100° C. for 1 h and TLC analysis showed complete conversion of starting material. After completion the reaction mixture was cooled to 0° C. and diluted with ice cold water (30 mL, 100 vol.), and then extracted with dichloromethane (20 mL). The organic phase was then washed twice with water (2×10 mL) and dried over anhydrous sodium sulfate. The solvent was then removed under vacuum to provide Compound 4b as light yellow solid. (96 mg, 58%). $^1$H NMR (400 MHz, CDCl3): δ 3.64 (s, 3H), 2.88 (dd, J=12.8 Hz, 4.8 Hz, 1H), 2.48 (t, J=11.6 Hz, 1H), 2.4-0.85 (m, 30H), 0.69 (s, 3H); 13C NMR (100 MHz, CDCl3): δ 210.7, 209.8, 174.1, 54.3, 51.0, 49.0, 48.4, 47.3, 44.5, 42.4, 42.3, 42.2, 38.4, 36.3, 34.9, 34.7, 30.6, 30.5, 27.7, 24.3, 21.9, 21.6, 17.9, 11.6; ESIMS for C25H38O4 m/z 420.7 [M+18]+.

Example 2. Synthesis of UDCA and TUDCA from Compound 4b

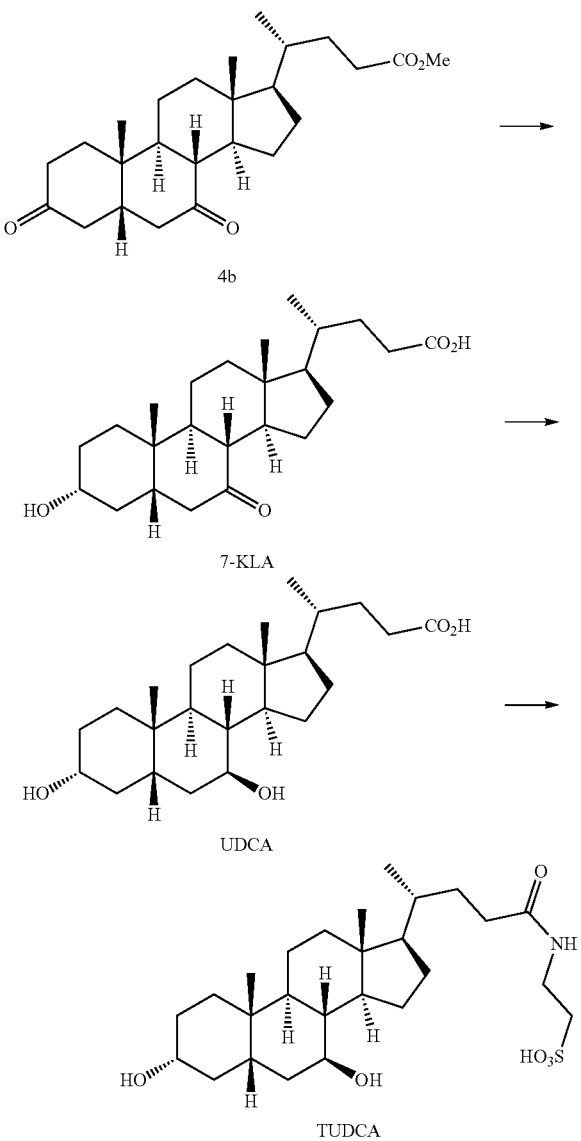

Synthesis of 7-KLA from Compound 4b: A 250 mL round bottom flask equipped with a stirring bar was charged with Compound 4b (40 g, 99.3 mmol) and THF (400 mL, 10 vol.) under a nitrogen atmosphere. The solution was cooled to −78° C. and lithium tri-tert-butoxyaluminum hydride (119.2 mL, 1.2 equiv., 1M solution in THF) was added over a period of 15 minutes. The reaction was continued for 5 h at −78° C., at which point TLC analysis showed complete conversion of starting material. The reaction was quenched with aq. ammonium chloride solution (at −78° C.) and then it was warmed to room temperature, where it was held with continued stirring for 0.5 h. The product was extracted into ethyl acetate (2×250 mL). The combined organic fractions were concentrated under vacuum to obtain the methyl ester of 7-KLA (42 g crude) as a light-brown solid. $^1$H NMR (400 MHz, CDCl$_3$): δ 3.65 (s, 3H), 3.66-3.62 (m, 1H), 2.85 (dd, J=12.4 Hz, 5.9 Hz, 1H), 2.42-2.30 (m, 2H), 2.28-2.12 (m, 3H), 2.02-1.62 (m, 10H), 1.50-1.02 (m, 13H), 1.02-0.76 (m, 4H), 0.65 (s, 3H); ESIMS for $C_{25}H_{40}O_4$ m/z 405.8 [M+H]$^+$.

The methyl ester of 7-KLA was charged to a 500 mL single neck round bottom flask along with isopropanol (IPA, 210 mL, 5 vol.) at room temperature, resulting in a solution. 10% aq. sodium hydroxide solution (210 mL, 5 vol.) was added and the resulting mixture was stirred at 60° C. for 2 h. At this point, TLC analysis showed complete conversion of starting material. The IPA was evaporated under reduced pressure and the resulting solution was washed with ethyl acetate (2×50 mL). The pH of aqueous layer was adjusted to 2-3 by using 2N hydrochloric acid solution (160 mL) and the resulting solid was filtered. It was washed with water (100 mL) and dried under vacuum to obtain a light-brown solid (38 g). This solid was recrystallized from in 5% MeOH-EtOAc to obtain 7-KLA as an off-white solid (29 g, 70% overall yield for the two steps). $^1$H NMR (400 MHz, CDCl$_3$): δ 3.64-3.62 (m, 1H), 2.88 (dd, J=12.3 Hz, 5.9 Hz, 1H), 2.48-2.39 (m, 2H), 2.36-2.19 (m, 3H), 2.06-1.69 (m, 10H), 1.52-1.09 (m, 13H), 1.02-0.87 (m, 4H), 0.68 (s, 3H); ESIMS for $C_{24}H_{38}O_4$ m/z 390.0 [M]$^+$.

Synthesis of UDCA from 7-KLA: 7-KLA (12 g, 30.72 mmol) was charged to a 2-liter stainless steel autoclave along with IPA (960 mL, 80 vol). Potassium tert-butoxide (5.86 g, 1.74 equiv.) was added and the solution was stirred for 0.5 h at room temperature. Anhydrous Raney Nickel was prepared upon repeated suspension of an aqueous slurry of Raney Nickel with IPA under nitrogen and removing the supernatant by decantation. The resulting anhydrous Raney Nickel (20 g) was added to the solution of 7-KLA and the resulting mixture was stirred at 40° C. under 500 psi hydrogen pressure for 5 h. At this point, TLC analysis showed complete conversion of starting material. The solution was filtered through a thin pad of CELITE® (silica), the IPA solvent was evaporated under reduced pressure and the residue was diluted with water (240 mL, 20 vol.). The pH was adjusted to 1 by adding 6N hydrochloric acid and the resulting mixture was stirred for 1 h at room temperature. The solid was filtered, washed with water (5 vol), then with methyl tert-butyl ether (MTBE, 2 vol) and then it was dried under vacuum to obtain UDCA as a white solid (9 g, 75% yield).

Purification of impure UDCA: UDCA (38 g) was dissolved in anhydrous DMF (380 mL, 10 vol) and hexamethyldisilazide (HMDS, 76 mL, 2 vol.) was added. The resulting mixture was stirred at 55-60° C. for 2 h, at which point TLC analysis showed complete conversion (a clear solution was observed). Thereafter, the reaction mixture was cooled to 0-4° C. where it was held for 4 h. The resulting solid was filtered, washed with cold (0-5° C.) anhydrous DMF (76 mL, 2 vol.) and the resulting solid product was dried under vacuum.

The isolated solid was suspended in 5% aq. HCl solution (pH 1, 190 mL, 5 vol.) and stirred at 50° C. for 0.5 h. The reaction mixture was then cooled to 10° C. in an ice water bath and filtered. The solid product was washed with cold water (0-5° C., 190 mL, 5 vol) and then dried under vacuum to obtain purified UDCA as a white solid (28 g, 74% recovery). $^1$H NMR (400 MHz, CD$_3$OD): δ 3.52-3.42 (m, 2H), 2.38-2.28 (m, 1H), 2.26-2.14 (m, 1H), 2.04 (m, 1H), 1.92-1.78 (m, 5H), 1.64-0.92 (m, 24H), 0.70 (s, 3H); $^{13}$C NMR (100 MHz, CD$_3$OD): δ 176.17, 70.19, 70.00, 55.56, 54.62, 42.85, 42.57, 42.11, 39.64, 38.78, 36.68, 36.08, 34.74, 34.18, 33.24, 30.43, 30.08, 29.11, 27.69, 26.00, 22.02, 20.47, 17.01, 10.73; ESIMS for $C_{24}H_{40}O_4$ m/z 391.7 [M−H]$^+$.

Synthesis of TUDCA from UDCA: UDCA (5 g, 12.736 mmol) was charged to a 100 mL single neck round bottom flask. Acetone (30 mL, 6 vol) was added, resulting in a solution. Triethylamine (TEA, 1.7 mL, 0.97 equiv.) was added and the solution was cooled to 0° C. Ethyl chloroformate (1.34 g, 0.97 equiv.) was added and the resulting mixture was stirred for 4 h at room temperature under N$_2$ atmosphere. The reaction mixture was filtered to remove triethylamine hydrochloride and the filtrate was added dropwise to an aqueous solution of taurine sodium salt (prepared by reacting 1.9 g taurine with 0.6 g NaOH in 3.7 mL water) at room temperature over a period of 20 minutes. The reaction was continued for another 1 h at room temperature, at which point TLC analysis showed complete conversion.

Conc. HCl (1.5 mL), was added at room temperature to adjust the pH to ~1. After stirring for 1 h, the resulting solid was filtered (0.9 g). The filtrate was diluted with acetone, stirred for 36 h at room temperature and the resulting solid was filtered, washed with acetone (10 mL) and dried under vacuum to obtain TUDCA as a white solid (5.1 g, 80% yield). $^1$H NMR (400 MHz, CD$_3$OD): δ 3.62 (t, J=6.8 Hz, 2H), 3.52-3.42 (m, 2H), 2.97 (t, J=6.8 Hz, 2H), 2.38-2.28 (m, 1H), 2.20-2.10 (m, 1H), 2.08-2.00 (m, 1H), 1.92-1.75 (m, 5H), 1.65-0.96 (m, 21H), 0.95 (s, 3H), 0.70 (s, 3H); $^{13}$C NMR (100 MHz, CD$_3$OD): δ 177.97, 72.12, 71.96, 47.45, 56.34, 50.78, 44.79, 44.46, 43.99, 41.52, 40.69, 38.56, 37.96, 37.47, 36.89, 36.07, 35.15, 33.34, 33.18, 30.99, 29.63, 27.91, 23.93, 22.37, 18.96, 12.64; ESIMS for $C_{24}H_{40}O_4$ m/z 499.1 [M−H]$^+$.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A compound of Formula I:

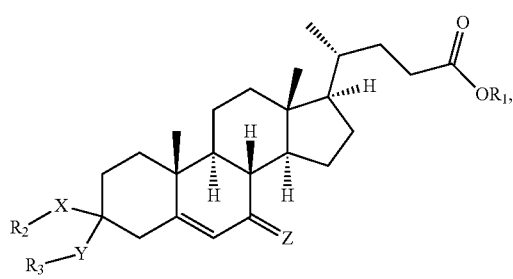

Formula I or a carboxylate salt thereof,
wherein:
a) X is oxy, thio, or N(R$_4$);
b) Y is oxy or thio;
c) Z is oxo;
d) R$_1$ is hydrogen, a counterion when the compound is a carboxylate salt, optionally substituted C$_{1-20}$ alkyl, or optionally substituted aryl;
e) R$_2$, and R$_3$ are independently selected from optionally substituted C$_{1-20}$ alkyl and optionally substituted aryl;
f) R$_2$ and R$_3$ optionally are joined to form with X and Y a spirofused heterocyclic ring at the 3-position of Formula I; and
g) R$_4$ is H, optionally substituted C$_{1-20}$ alkyl, or optionally substituted aryl.

2. The compound of claim 1, wherein X is oxy and Y is oxy.

3. The compound of claim 1, wherein X is oxy, Y is oxy, and R$_2$ and R$_3$ are joined to form with X and Y a spirofused heterocyclic ring at the 3-position of Formula I.

4. The compound of claim 1, represented by Formula Ia or Formula Ib:

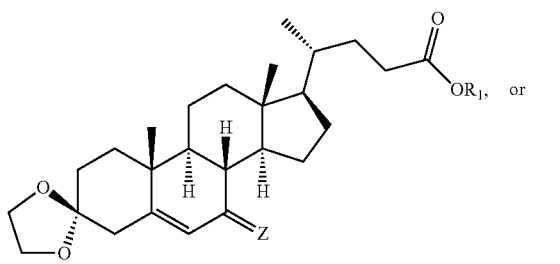

Formula Ia

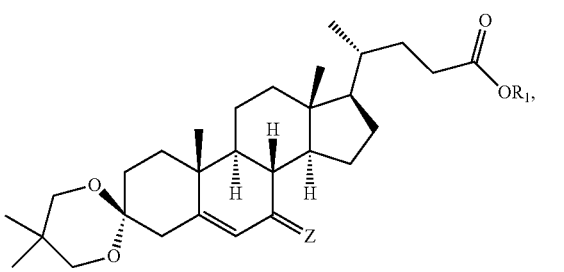

Formula Ib or a carboxylate salt thereof, wherein R$_1$ is hydrogen or C$_{1-6}$ alkyl or a counterion when the compound is a carboxylate salt.

5. The compound of claim 4, of Formula Ia, wherein R$_1$ is methyl.

6. The compound of claim 4, of Formula Ia, wherein R$_1$ is ethyl.

7. The compound of claim 4, of Formula Ib, wherein R$_1$ is methyl.

8. The compound of claim 4, of Formula Ib, wherein R$_1$ is ethyl.

9. A compound of Formula III:

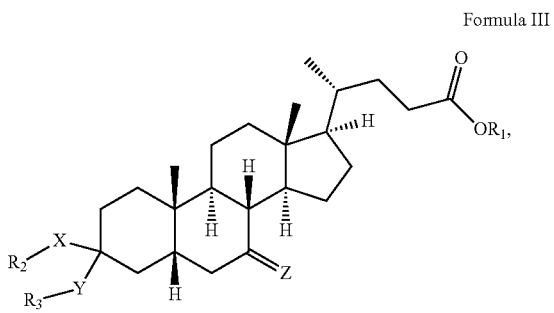

Formula III wherein:
a) X is oxy, thio, or N(R$_4$);
b) Y is oxy or thio;
c) Z is oxo;
d) R$_1$ is optionally substituted C$_{1-20}$ alkyl, or optionally substituted aryl;
e) R$_2$, and R$_3$ are independently selected from optionally substituted C$_{1-20}$ alkyl and optionally substituted aryl;
f) R$_2$ and R$_3$ optionally are joined to form with X and Y a spirofused heterocyclic ring at the 3-position of Formula III; and
g) R$_4$ is H, optionally substituted C$_{1-20}$ alkyl, or optionally substituted aryl.

10. The compound of claim 9, wherein X is oxy and Y is oxy.

11. The compound of claim 9, wherein X is oxy, Y is oxy, and R$_2$ and R$_3$ are joined to form with X and Y a spirofused heterocyclic ring at the 3-position of Formula III.

12. A compound of Formula IIIa or Formula IIIb:

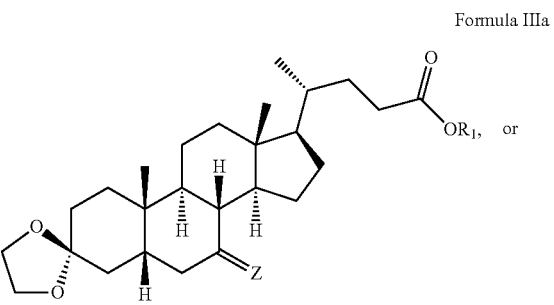

Formula IIIa

Formula IIIb

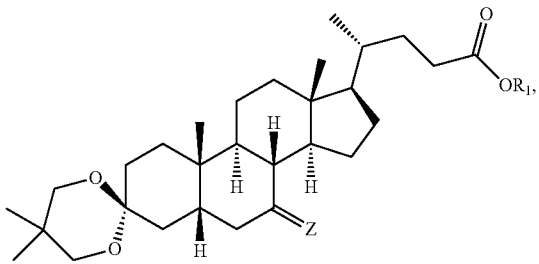

or a carboxylate salt thereof,
wherein:
a) Z is oxo; and
b) $R_1$ is hydrogen, a counterion when the compound is a carboxylate salt, optionally substituted $C_{1-20}$ alkyl, or optionally substituted aryl.

13. The compound of claim 12, of Formula IIIa, wherein $R_1$ is methyl.

14. The compound of claim 12, of Formula IIIa, wherein $R_1$ is ethyl.

15. The compound of claim 12, of Formula IIIb, wherein $R_1$ is methyl.

16. The compound of claim 12, of Formula IIIb, wherein $R_1$ is ethyl.

17. A method of converting the compound of claim 1 to ursodeoxycholic acid or a carboxylate salt at the 24-position thereof, comprising:
  a) reducing the 5,6-alkene double bond to a dihydro product with 5β stereochemistry;
  b) hydrolyzing the electronegative groups at the 3-position to produce a 3-ketone;
  c) reducing the 3-ketone to 3α-hydroxyl;
  d) reducing the 7-ketone to 7β-hydroxyl; and
  e) when $R_1$ is alkyl or aryl, hydrolyzing the —$CO_2R_1$ ester to a carboxylic acid;
  wherein steps (a)-(e) may be carried out sequentially, simultaneously, or in any order, except that step (b) must be performed before step (c).

* * * * *